United States Patent [19]
Brassil et al.

[11] Patent Number: 5,967,779
[45] Date of Patent: Oct. 19, 1999

[54] ABRASION HAND PIECE FOR USE WITH ABRASION SYSTEM

[75] Inventors: John Michael Brassil, Glenview; Shu Kun Chang, Evanston, both of Ill.; Roberto Giovanni Fraquelli, London, United Kingdom; Gary Neilsson, Mundelein, Ill.

[73] Assignee: Dentsply Research & Development Corp., Los Angeles, Calif.

[21] Appl. No.: 08/951,948

[22] Filed: Oct. 17, 1997

[51] Int. Cl.⁶ ..................................................... A61C 3/02
[52] U.S. Cl. ................................................................. 433/88
[58] Field of Search ............................... 433/80, 82, 88; 51/319, 320, 321

[56] References Cited

U.S. PATENT DOCUMENTS

| | | | |
|---|---|---|---|
| 515,845 | 10/1894 | Bailey | 433/88 |
| 2,661,537 | 12/1953 | Angell | 32/58 |
| 2,874,470 | 2/1959 | Richards | 433/88 X |
| 3,972,123 | 8/1976 | Black | 32/58 |
| 4,214,871 | 7/1980 | Arnold | 433/88 X |
| 4,340,366 | 7/1982 | Heil | 433/82 |
| 4,412,402 | 11/1983 | Gallant | 51/439 |
| 4,482,322 | 11/1984 | Hain et al. | 433/88 |
| 4,487,582 | 12/1984 | Warrin | 433/88 |
| 4,492,575 | 1/1985 | Mabille | 433/88 |
| 4,595,365 | 6/1986 | Edel et al. | 433/88 X |
| 4,733,503 | 3/1988 | Gallant et al. | 51/410 |
| 4,893,440 | 1/1990 | Gallant et al. | 51/436 |
| 5,059,121 | 10/1991 | Schulz et al. | 433/88 |
| 5,062,796 | 11/1991 | Rosenberg | 433/88 X |
| 5,203,698 | 4/1993 | Blake et al. | 433/88 |
| 5,275,561 | 1/1994 | Goldsmith | 473/216 |
| 5,330,354 | 7/1994 | Gallant | 433/88 |
| 5,334,016 | 8/1994 | Goldsmith et al. | 433/29 |
| 5,334,019 | 8/1994 | Goldsmith et al. | 433/88 |
| 5,336,202 | 8/1994 | Bailly et al. | 433/88 X |
| 5,350,299 | 9/1994 | Gallant | 433/88 |
| 5,525,058 | 6/1996 | Gallant et al. | 433/88 |
| 5,618,177 | 4/1997 | Abbott | 433/88 |

OTHER PUBLICATIONS

W.H. McGehee, et al, A Textbook of Operative Dentistry, 1956, pp. 266–273.

Bonner, Phillip, Air Abrasion: The New "Drill–Less" Dentistry Today, Sep. 1997 issue, pp. 58–65.

Goldstein, Ronald, et al., Air–Abrasive Technology: Its New Role in Restorative Dentistry, JADA, vol. 15, May 1994, pp. 551–557.

*Primary Examiner*—Nicholas D. Lucchesi
*Attorney, Agent, or Firm*—Douglas J. Hura; James B. Bieber

[57] ABSTRACT

An abrasion hand piece for use with an air abrasion system to perform dental procedures. The hand piece is adapted for connection to the air abrasion system by a hose and has a body member which allows tips to be releasably attached thereto. The releasable tip feature allows the body member to be used with a number of different tips, thereby reducing the number of tools that the dentist must have on hand and must sterilize between procedures. The tips have an outer coating which is softer and warmer to the patient when placed in the mouth. The outer coating is color coded so that the orifice size of the tips may be readily identified. An illumination device is attached to the hand piece to allow the dentist to better monitor the procedure and to provide for aiming the hand piece at the desired tooth area. The hand piece with releasable tip feature, when used with an abrasion system having a continuous purge, allows the tip to be removed and used later during the same procedure without creating a crosstalk or backflow situation.

10 Claims, 2 Drawing Sheets

ABRASION HAND PIECE FOR USE WITH ABRASION SYSTEM

FIELD OF THE INVENTION

The present invention generally relates to dental apparatus, and more particularly relates to hand pieces for use with air abrasion systems.

BACKGROUND OF THE INVENTION

Air abrasion systems are generally known which deliver a mixture of abrasive material and pressurized gas to perform tooth reduction procedures. Tooth reduction is commonly performed to remove tooth decay and may involve cutting, excavating, or etching of the enamel and dentin layers of the tooth. Procedures using air abrasion systems are similar to sand-blasting operations in that particles of abrasive material are propelled at an elevated velocity toward the tooth area so that the particles cut the tooth.

Air abrasion systems are commonly attached by a hose to an abrasion hand piece which directs the gas-abrasive material mixture toward the target area inside the patient's mouth. The abrasive hand pieces typically have a nozzle orifice at one end thereof which directs the mixture. The dentist holds the hand piece and aims the nozzle orifice at the desired location so that the affected tooth structure is reduced.

Unfortunately, conventional abrasion hand pieces cause discomfort to the patient. Previous hand pieces typically have a metal tip which is inserted inside the mouth during dental procedures. The metal tip has a hard outer surface which the patient may accidentally bite and which uncomfortably rests inside the patient's mouth. Furthermore, the backside of the tip is often used to retract the cheek, lips, and tongue of the patient. When used in this manner, the metal tip creates a localized point of pressure at the area of contact with the mouth which is uncomfortable to the patient.

A further problem with conventional abrasion hand pieces is that they make it difficult to determine which hand piece is intended for use during a particular dental procedure. The appearance of conventional abrasion hand pieces are similar so that hand pieces having nozzles disposed at similar angles appear to be identical, even though they may have nozzle orifices sized for different dental procedures. As a result, conventional abrasion hand pieces make it difficult to select the appropriate hand piece for a particular procedure from a group of hand pieces.

Conventional abrasion hand pieces are also overly difficult to maneuver. The dentist must frequently reposition the tip of the abrasion hand piece during a dental procedure. To redirect the tip, the dentist must typically move the entire hand piece by, for example, rolling or repositioning the hand piece in his or her hand. Furthermore, conventional abrasion hand pieces are typically connected to a hose which tends to restrict or limit such repositioning, making it awkward to redirect the tip.

Conventional abrasion hand pieces are further awkward to hold. Abrasion hand pieces typically have an outer surface similar to that of a pen. The abrasion hand piece is typically held between the thumb and forefinger, with a rear portion of the hand piece resting near the base of the thumb at a specific contact point. Accordingly, conventional hand pieces are easily dropped, especially if the hand piece slips from between the thumb and forefinger.

Conventional abrasion hand pieces, when used with conventional abrasion systems, have a problem of build-up of residual abrasive material inside the hand piece. When convention abrasion systems finish delivering a blast of abrasive material, some material remains in the hand piece. This is detrimental because subsequent blasts of abrasive material are resisted by the residual material, thereby lowering the velocity of the subsequent blasts to create puffs of abrasive material which are dispersed outside the patient's mouth. As a result, when a hand piece is used with a conventional system, the hand piece may contain residual abrasive material and therefore must be replaced or cleaned before subsequent use.

SUMMARY OF THE INVENTION

A general aim of the present invention is to provide an abrasion hand piece which is easier to manipulate and redirect during dental procedures.

It is also an object of the present invention to provide an abrasion hand piece which better fits the hand of the dentist and does not easily slip.

It is a further object of the present invention to provide an abrasion hand piece which is more comfortable to the patient.

Still another object of the present invention is to provide an abrasion hand piece set having easily identifiable tools.

In light of the above, the present invention provides an abrasion hand piece which includes a swivel connection mid-way through the body portion. The swivel connection allows the neck end of the body member nearest the tip to rotate with respect to the base end of the body member. In operation, the base end of the abrasion hand piece rests near the part of the hand connecting the thumb and forefinger while the rotatable neck portion of the body member is grasped between the thumb and forefinger. To redirect the tip, the dentist simply needs to move the thumb and forefinger, thereby rotating the neck portion of the hand piece.

The present invention further provides an improved abrasion hand piece having an outer coating for improving comfort to the patient and identification of nozzle orifice size. The outer coating provides a softer surface which is inserted into the mouth of the patient. The tip, therefore, rests more comfortably in the patient's mouth and reduces pain to the patient when used for retraction or during accidental bites. Moreover, when the tips are detachable as noted above, the outer coating may be colored to identify specific tips. For example, when a dentist desire, to use tips having different orifice sizes during a dental procedure, the different tips can be easily identified by a colored outer coating. As a result, the dentist is able to more quickly and easily locate the appropriate tip.

The present invention also provides an improved abrasion hand piece including an ergonomically designed outer surface. The body member of the hand piece has a contoured outer surface which is configured to better conform to the hand of the dentist. A middle portion of the body member bulges to a larger diameter, making it more difficult for the hand piece to slide through the hand of the dentist. The contoured outer surface therefore not only makes the hand piece easier to grasp and hold, but also resists slipping due to the irregular shape It is also a feature of the present invention to provide an abrasion hand piece which does not clog with residual abrasive material when used with an abrasion system having a continuous purge line. The continuous purge clears the hand piece of residual abrasive material, thereby allowing the hand piece to be used with different removable tips without restricting delivery of abrasive material.

These and other aims, objectives, and advantages of the invention will become more apparent from the following detailed description when taken in conjunction with the accompanying drawings.

Figure 1:
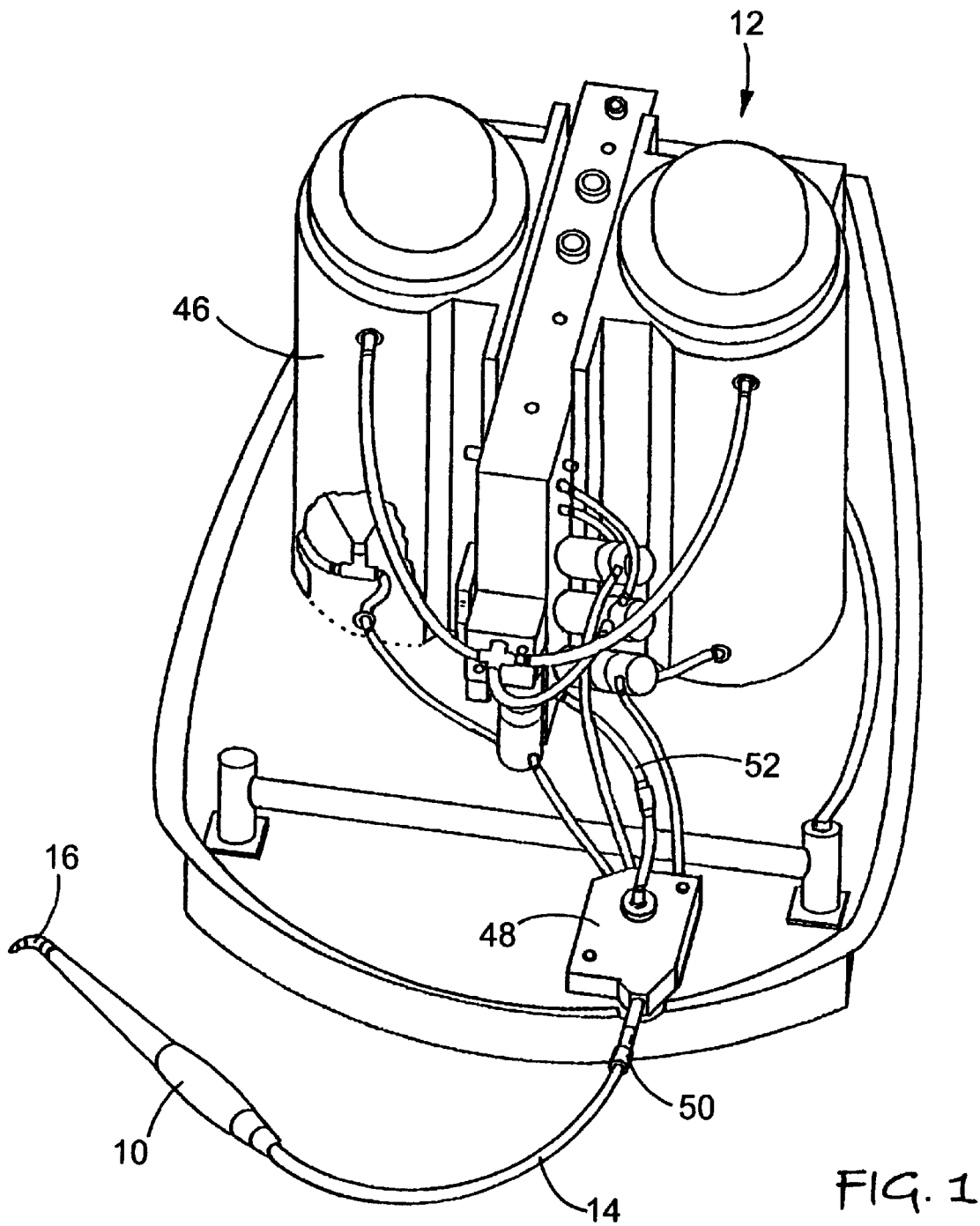
FIG. 1 is a perspective view of an abrasion hand piece in accordance with the present invention attached to an air abrasion system.

While the invention is susceptible of various modifications and alternative constructions, certain illustrative embodiments thereof have been shown in the drawings and will be described below in detail. It should be understood, however, that there is no intention to limit the invention to the specific forms disclosed, but on the contrary, the invention is to cover all modifications, alternative constructions, and equivalents falling within this spirit and scope of the invention as defined by the appended claims.

DETAILED DESCRIPTION OF THE PREFERRED EMBODIMENT

Referring now to the drawings, FIG. 1 shows an abrasion hand piece 10 attached to an air abrasion system 12 by a hose 14. The air abrasion system 12 delivers a mixture of abrasive material with pressurized gas which travels through the hose 14 and is discharged by the hand piece 10. The hand piece 10 has a tip 16 which directs the gas-abrasive mixture toward the desired tooth structure. The hand piece 10 to deliver aluminum oxide, however other abrasive materials may be used with the hand piece in accordance with the present invention.

Figure 3:
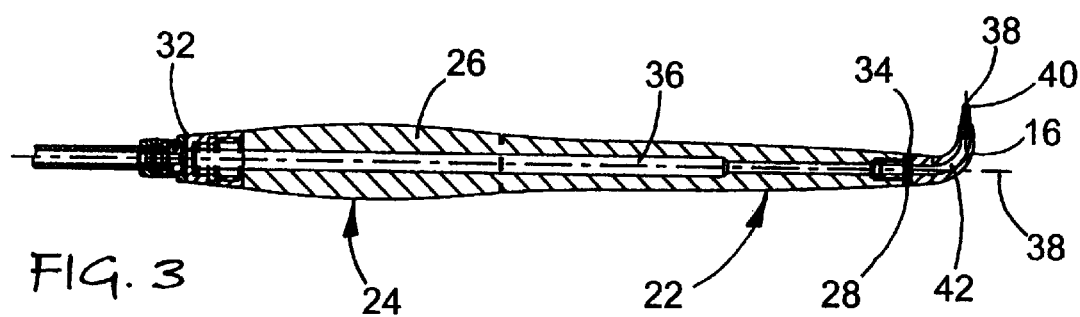
FIG. 3 is a cross sectional view of the hand piece taken along line 3—3 of FIG. 2.

In greater detail, the abrasion hand piece 10 comprises a body member 26 and tip 16. The body member 26 extends along an axis 30 and has base and neck ends 32, 34 (FIG. 3). A central bore 36 extends through the body member 26 from the base end 32 to the neck end 34. The tip 16 begins at the neck end 34 and has a nozzle orifice 38 disposed at a discharge end 40. A central passage 42 extends through the tip 16 and leads to the nozzle orifice 38. The body member 26 and tip 16 are preferably formed from metal material, most preferably aluminum for the body member and cast aluminum for the tip. In the preferred embodiment, a carbide insert forms the nozzle orifice 38 to resist wear.

In operation, the gas-abrasive mixture from the abrasion system 12 is delivered through the hose 14 to the abrasion hand piece 10. The gas-abrasive mixture travels through the central bore 36 of the body member 26 to the central passage 42 of the tip 16, whereupon the mixture is discharged through the nozzle orifice 38.

Figure 4:
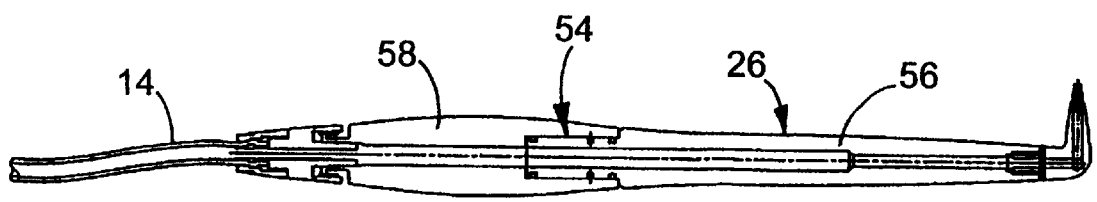
FIG. 4 is a cross-sectional view of a hand piece having a swivel connection in accordance with the present invention.

The hand piece 10 includes a swivel connection 54 for facilitating repositioning of the hand piece during a dental procedure. It will be appreciated that the dentist often needs to reposition the hand piece 10 during a dental procedure. The hand piece 10 is, however, attached to the hose 14 which resists certain movements of the hand piece. As best shown in FIG. 4, the body member 26 comprises first and second portions 56, 58 joined by the swivel connection 54. As a result, the first portion 56 of the body member 26 may be rotated with respect to the second portion 58. The swivel connection 54 therefore makes repositioning of the hand piece 10 easier since the dentist can rotate the first portion 56 without disturbing the second portion 58 attached to the hose 14.

Figure 2:
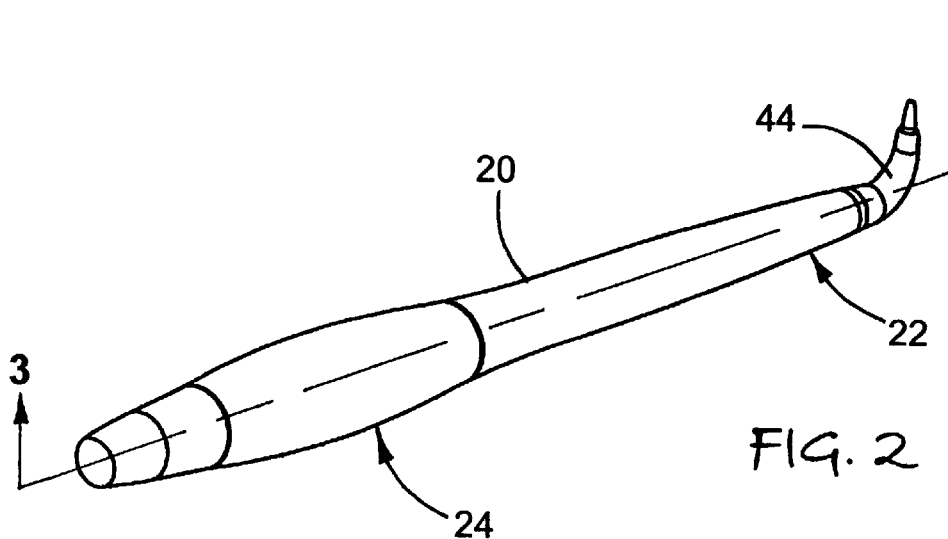
FIG. 2 is an enlarged perspective view of the hand piece shown in FIG. 1.

As best shown in FIG. 2, the abrasion hand piece 10 includes a contoured outer surface 20 for improved gripping characteristics. The illustrated embodiment shows an abrasion hand piece 10 having a slightly tapered neck portion 22 and a bulging base portion 24. The neck portion 22 carries the tip 16, which is inserted into the mouth during dental procedures. Base portion 24 rests in the portion of the hand connecting the thumb and forefinger, while the neck portion 22 is pinched between the thumb and forefinger. The increased diameter of the bulge in the base portion 24 more closely conforms to the shape of the hand and therefore is easier to grasp and resists slippage found in conventional, uniform outer diameter hand pieces.

The tip 16 of the abrasion hand piece 10 is removable for allowing the body member 26 to be used with a variety of tips. As best shown in FIG. 3, the neck and base portions 22, 24 of the abrasion hand piece 10 form the body member 26. The tip 16 is releasably connected to the body member 16 by attachment means 28. As a result, the tip 16 may be removed from the body member 26 and replaced with a different tip (not shown). As illustrated in FIG. 3, the attachment means 28 comprises mating threads, although other releasable connections may be used in accordance with the present invention.

From the foregoing it will be appreciated that the abrasion hand piece 10 has a body member 26 which can be used with a plurality of different tips during a dental procedure. This feature is significant because nozzle orifices come in a number of different sizes and discharge angles to perform different types of tooth abrasion. For example, it has been found that tips for use with aluminum oxide should have nozzle orifices ranging from at least about 0.015" to no more than about 0.027". Nozzle orifices smaller than about 0.015" tend to clog the orifice, while sizes greater than about 0.027" make holes in the tooth of a size which approaches that of drilled holes, and therefore defeats the purpose for using air abrasion to perform the procedure.

Orifice sizes within the above range are used to perform certain procedures. For example, orifice sizes near the lower end of the range are used to cut smaller tooth areas, while larger sizes cut larger areas. Furthermore, tips having different discharge angles are used to reach different tooth structures inside the mouth. Angles from 0 to 120 degrees are typically provided. Accordingly, a multitude of nozzle orifice sizes and angles are used to complete a single dental procedure.

More specifically, it has been found that a number of standard orifice sizes and angles within the given ranges adequately provide for the different types of procedures. Standard orifice sizes of 0.015", 0.018", and 0.027" allow the dentist to perform small, medium, and large tooth cuts, however different orifice sizes within the range may also be used in accordance with the present invention. Similarly, while the present invention contemplates all angles within the 0 to 120 degree range, standard discharge angles of 45, 90, and 120 degrees have been found to provide an adequate selection for reaching all areas of the mouth.

In accordance with significant aspects of the present invention, the tip 16 has an outer coating 44 for reducing discomfort to the patient during dental procedures. As best shown in FIG. 2, the outer coating 44 covers entire tip 16 and is formed from a relatively soft and formable material such as soft silicones, fluorinated rubber compounds, nylons, thermoplastics and the like, to provide a more comfortable and warmer feeling surface than conventional metal tips.

In the preferred embodiment, the outer coating 44 is color coded so that the orifice size of the tip 16 is more readily identifiable. As noted above, a number of different orifice sizes and angles may be required during a dental procedure. In general, the tips have a similar appearance and are typically distinguishable only by the angle of discharge. A number of different tips having different orifice sizes, however, may have the same discharge angle and therefore are difficult to distinguish. Accordingly, the outer coating 44 of each tip 16 has a specific color which identifies the type of tip. In the present invention, for example, tips having an orifice size of 0.015" all have an outer coating of the same color, regardless of discharge angle. The dentist may then easily identify the tip having the appropriate orifice size from the color of the outer coating and can select the appropriate discharge angle from the appearance of the tip.

In one embodiment of the present invention, illumination means are attached to the hand piece 10 for allowing the dentist to better view the dental procedure and to provide means for aiming the tip 16 at the desired tooth area. The illumination means preferably comprises a fiber optic source directing light through a fiber optic cable attached to the hand piece 10 with cable attachment means. A cable attachment means is located near the nozzle orifice so that the end of the fiber optic cable aims substantially in the same direction as the nozzle orifice. As a result, the light from the illumination means illuminates the mouth to enable the dentist to better view the procedure. In addition, the light may be focused to illuminate a point on the particular tooth area to be abraded, thereby providing means for aiming the hand piece 10 at the desired area.

The replaceable tip feature, in combination with an air abrasion system 12 having a continuous purge feature, allows the same body members 26 to be used with a variety of tips 16 without creating a crosstalk situation. Crosstalk occurs when residual abrasive material remains in the abrasion system 12, hose 14, or hand piece 10 after completing delivery of the air-abrasive mixture. When the dentist desires to deliver a subsequent blast of the mixture, the residual material resists the subsequent flow thereby reducing the pressure of the subsequent blast. As a result, the subsequent blast of mixture is at a lower velocity which may not effectively cut the tooth. In addition, if the dentist has switched the type of abrasive material to be delivered, the initial blast includes the previous (and therefore incorrect) abrasive material.

To avoid this problem, the present invention includes an air abrasion system 10 having a continuous purge which allows the same body member 26 to be used with different tips and abrasive materials without creating crosstalk. The abrasion system 10 mixes pressurized gas with abrasive material from a dispensing chamber 46. The dispensing chamber delivers the mixture to a mixing block 48 having an outlet connection 50. The outlet connection 50 is attached to the hose 14 which delivers the mixture to the abrasive hand piece 10.

In accordance with significant aspects of the present invention, the air abrasion system 12 incorporates a purge line 52 through which gas is continuously delivered. The purge line 52 extends from the pressurized gas source to the mixing block 48 of the abrasion system 12. Gas is continuously fed through the purge line 52 and therefore ejects any residual abrasive material from the hand piece 10 between blasts. It will be appreciated therefore that the tip 16 attached to the body member 26 of the hand piece 10 is purged of residual abrasive material and therefore may be removed and used later without creating a crosstalk situation.

From the foregoing, it will be apparent that the present invention brings to the art an abrasion hand piece which is easier to work with during dental procedures. The hand piece has a contoured outer surface which better conforms to the hand of the dentist. Furthermore, the hand piece has a swivel connection which allows fingertip redirection of the hand piece. The hand piece of the present invention also incorporates removable tips having a coating of soft material. The removable tips allow the same body member of the hand piece to be used with a number of different tips, thereby reducing the tool inventory of the dentist. The outer coating of the tips improves patient comfort and allows the tips to be color coded for easy identification.

What is claimed is:

1. An abrasion hand piece for use with an air abrasion system to perform dental procedures, the hand piece adapted for releasable attachment to a hose leading to the air abrasion system, the hand piece comprising:

an elongate body member extending along an axis having base and head ends, a central bore extending through the body member along the axis, and first and second portions connected by means for swiveling the first portion with respect to the second portion, and a tip removably attached to the head end of the body member with attachment means, the tip having a connection end and a discharge end, a central passage extending through the tip from the connection end to the discharge end, a nozzle orifice located at the discharge end having a given size, the nozzle orifice being disposed at an angle with respect to the axis.

2. The abrasion hand piece of claim 1 in which the body member is generally cylindrical and has a contoured outer surface.

3. The abrasion hand piece of claim 1 in which the tip has an outer coating of soft silicone material.

4. The abrasion hand piece of claim 1 in which the tip has an outer coating of fluorinated rubber compound material.

5. The abrasion hand piece of claim 1 in which the tip has an outer coating of nylon material.

6. The abrasion hand piece of claim 1 in which the tip has an outer coating of thermoplastic material.

7. The abrasion hand piece of claim 1 further comprising means for providing illumination attached to the tip.

8. An abrasion hand piece set for use with an air abrasion system to perform dental procedures, the abrasion hand piece set comprising:

an elongate body member extending along an axis having a central bore extending through the body member, and base and head ends; and first and second groups of tips adapted for releasable attachment to the body member, each tip of the first and second groups having a connection end and a discharge end, a central passage extending through the tip from the connection end to the discharge end, and a nozzle orifice on the discharge end disposed at an angle with respect to the axis of the body portion;

wherein the nozzle orifice of each tip in the first group of tips has a first diameter and the nozzle orifice of each tip in the second group of tips has a second diameter.

9. The abrasion hand piece set of claim 8 in which each tip in the first and second groups of tips has an outer coating, the outer coating of the first group having a first color and the outer coating of the second group having a second color.

10. An air abrasion system for delivering a mixture of pressurized gas and abrasive powder for use in dental procedures, the air abrasion system adapted to be attached to a pressurized gas source, the system comprising the combination of:

a dispensing chamber having a reservoir for holding a supply of abrasive powder, an inlet port adapted for fluid communication with the pressurized gas source, a powder outlet port, and motor means for advancing abrasive powder through the powder outlet ports;

a mixing block having a powder inlet port fluidly connected to the powder outlet port of the dispensing chamber, a purge port adapted for fluid connection to the pressurized gas source, and a common outlet connection; and an abrasion hand piece fluidly communicating with the outlet connection, the hand piece including a body member extending along an axis and having base and head ends, a central bore extending through the body member, and a tip removably attached to the head end of the body member and having a nozzle orifice for discharging the mixture of pressurized gas and abrasive powder;

wherein pressurized gas is supplied to the purge port for continuous flow through the mixing block, hose, and hand piece.

* * * * *